US008293385B2

(12) United States Patent
Hassan et al.

(10) Patent No.: US 8,293,385 B2
(45) Date of Patent: Oct. 23, 2012

(54) ORGANIC ELECTRONIC DEVICES USING PHTHALIMIDE COMPOUNDS

(75) Inventors: Azad M. Hassan, Los Angeles, CA (US); Mark E. Thompson, Anaheim, CA (US)

(73) Assignee: The University of Southern California, Los Angeles, CA (US)

( * ) Notice: Subject to any disclaimer, the term of this patent is extended or adjusted under 35 U.S.C. 154(b) by 0 days.

(21) Appl. No.: 12/854,297

(22) Filed: Aug. 11, 2010

(65) Prior Publication Data

US 2010/0300538 A1 Dec. 2, 2010

Related U.S. Application Data

(63) Continuation of application No. 11/783,817, filed on Apr. 12, 2007, now Pat. No. 7,790,298.

(60) Provisional application No. 60/792,120, filed on Apr. 13, 2006.

(51) Int. Cl.
*H01L 51/54* (2006.01)

(52) U.S. Cl. ........ 428/690; 428/917; 313/504; 313/505; 313/506; 257/40; 257/E51.05; 257/E51.026; 548/440

(58) Field of Classification Search .................. 428/690, 428/917; 313/504, 505, 506; 257/40, E51.05, 257/E51.026, E51.032; 548/440
See application file for complete search history.

(56) References Cited

U.S. PATENT DOCUMENTS

2002/0160227 A1* 10/2002 Kohama et al. ............... 428/690
2003/0137239 A1* 7/2003 Matsuura et al. ............. 313/503
2003/0168970 A1* 9/2003 Tominaga et al. ............ 313/504
2004/0209116 A1 10/2004 Ren
2005/0006641 A1 1/2005 Tung et al.

FOREIGN PATENT DOCUMENTS

JP 62-234062 * 10/1987
JP 2006045165 2/2006

OTHER PUBLICATIONS

Hasegawa et. al., Photophysical . . . Aromatic Polyimides,1993, J of Polymer Sci, Part B, Polymer Physics,1993, vol. 31, pp. 1617-1625.*
Drew et. al.,Chemiluminescent Organic Compounds . . . ,1937, Journal of the Chemical Society,pp. 16-26.*
Wantz et al., "Layered organic film growth by substrate temperature tuning for efficiency-enhanced OLEDs", Organic Electronics 7(1) 38-44, 2006.

(Continued)

*Primary Examiner* — Jennifer Chriss
*Assistant Examiner* — Gregory Clark
(74) *Attorney, Agent, or Firm* — Kenyon & Kenyon LLP

(57) ABSTRACT

Organic electronic devices comprising a phthalimide compound. The phthalimide compounds disclosed herein are electron transporters with large HOMO-LUMO gaps, high triplet energies, large reduction potentials, and/or thermal and chemical stability. As such, these phthalimide compounds are suitable for use in any of various organic electronic devices, such as OLEDs and solar cells. In an OLED, the phthalimide compounds may serve various functions, such as a host in the emissive layer, as a hole blocking material, or as an electron transport material. In a solar cell, the phthalimide compounds may serve various functions, such as an exciton blocking material. Various examples of phthalimide compounds which may be suitable for use in the present invention are disclosed.

23 Claims, 7 Drawing Sheets

OTHER PUBLICATIONS

Liou et al., "Electrochromic properties of novel strictly alternating poly(amine-amide-imide)s with electroactive triphenylamine moieties", European Polymer Journal, 42(7): 1533-1540, 2006.

PCT International Search Report mailed Sep. 3, 2007, PCT International Application No. PCT/US2007/009064.

Wang et al., "Luminescent properties of a novel naphthalimide-fluorene molecule", Synthetic Metals 150:33-38, 2005.

Kolosov et al., "1,8-naphthalimides in Phosphorescent Organic LEDs: The Interplay between Dopant, Exciplex, and Host Emission", J. Am. Chem. Soc. 124:9945-9954, 2002.

Demeter et al., "Comprehensive Model of the Photophysics of N-Phenylnaphthalimides: The Role of Solvent and Rotational Relaxation", J. Phys. Chem. 100:2001-2011, 1996.

Hasegawa, Photophysical Processes in Aromatic Polymides, J. Polymer Science, Part B, vol. 31, 1993, p. 1617-1625.

* cited by examiner

ORGANIC ELECTRONIC DEVICES USING PHTHALIMIDE COMPOUNDS

This application is a continuation of U.S. Ser. No. 11/783,817, filed on Apr. 12, 2007 now U.S. Pat. No. 7,790,298, which claims priority to U.S. Provisional Application Ser. No. 60/792,120 filed on Apr. 13, 2006, both of which are incorporated by reference in their entireties.

This invention was made with support from the United States Government, under Contract No. DE-FG02-03ER83813, awarded by the U.S. Dept. of Energy. The Government may have certain rights in this invention.

The claimed invention was made by, on behalf of, and/or in connection with one or more of the following parties to a joint university corporation research agreement: Princeton University, The University of Southern California, and the Universal Display Corporation. The agreement was in effect on and before the date the claimed invention was made, and the claimed invention was made as a result of activities undertaken within the scope of the agreement.

TECHNICAL FIELD

The present invention relates to organic electronic devices.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules. In general, a small molecule has a well-defined chemical formula with a single molecular weight, whereas a polymer has a chemical formula and a molecular weight that may vary from molecule to molecule. As used herein, "organic" includes metal complexes of hydrocarbyl and heteroatom-substituted hydrocarbyl ligands.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

SUMMARY

In one aspect, the present invention provides an organic electronic device comprising: an anode; a cathode; and an organic layer disposed between the anode and the cathode, wherein the organic layer comprises a phthalimide compound having the formula:

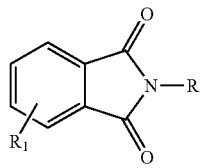

wherein $R_1$ represents one or more independently selected substitutions located on any position of the ring, wherein each substitution is a hydrogen, an alkyl moiety containing up to fifteen carbon atoms, or an aryl moiety, and wherein R is a phenyl group or a phthalimide-containing group.

In another aspect, the present invention provides an organic electronic device comprising: an anode; a cathode; and an organic layer disposed between the anode and the cathode, wherein the organic layer comprises a phthalimide compound having the formula:

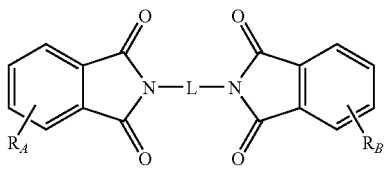

wherein $R_A$ represents one or more independently selected substitutions located on any position of the ring, wherein each substitution is a hydrogen, an alkyl moiety containing up to fifteen carbon atoms, or an aryl moiety, wherein $R_B$ represents one or more independently selected substitutions located on any position of the ring, wherein each substitution is a hydrogen, an alkyl moiety containing up to fifteen carbon atoms, or an aryl moiety, and wherein L is a 6-membered ring or a direct bond between the two phthalimide groups.

DETAILED DESCRIPTION

Figure 1:
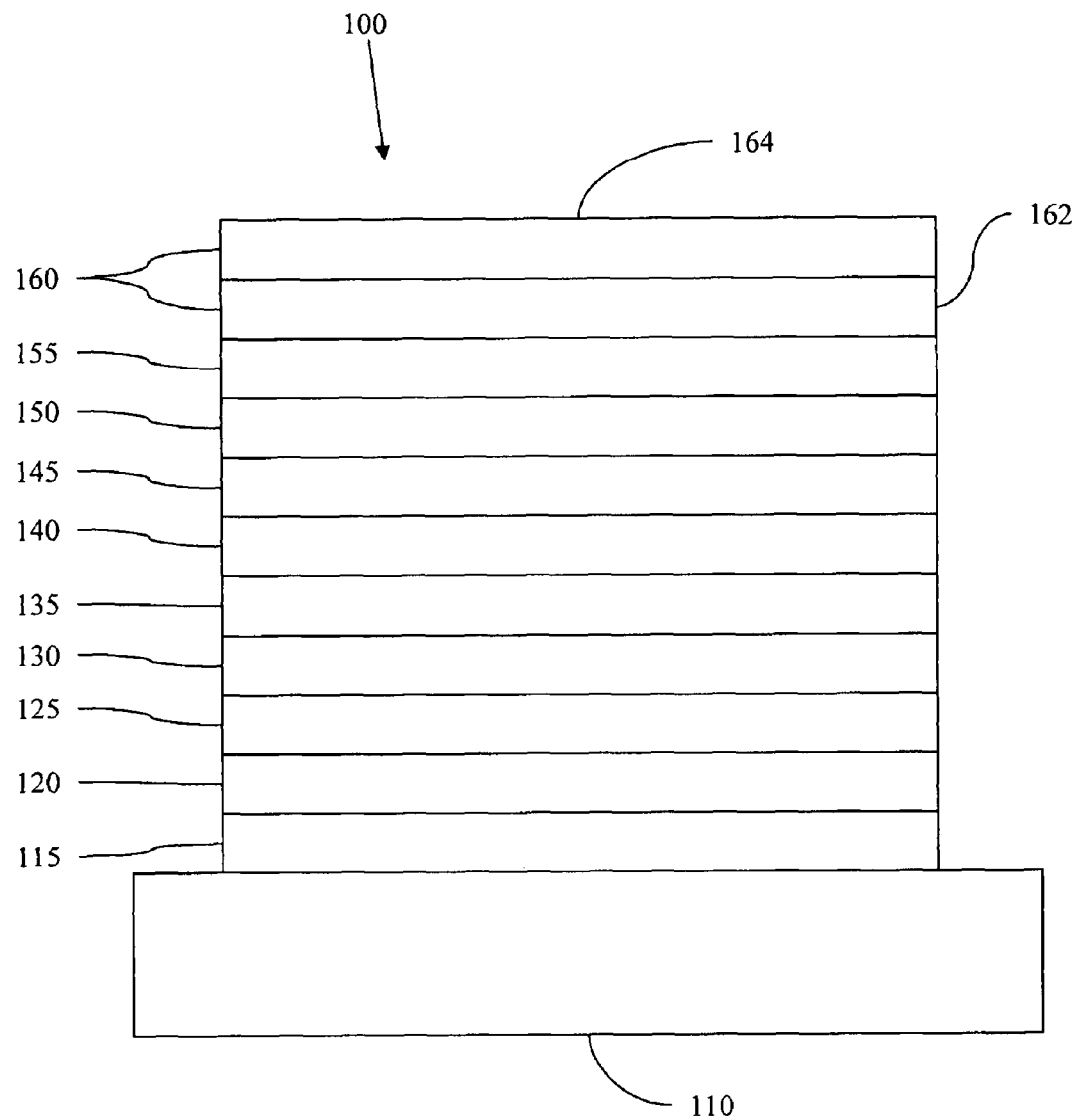
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered. undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 1, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that an organic material that exhibits phosphorescence at liquid nitrogen temperatures typically does not exhibit phosphorescence at room temperature. But, as demonstrated by Baldo, this problem may be addressed by selecting phosphorescent compounds that do phosphoresce at room temperature. Representative emissive layers include doped or un-doped phosphorescent organometallic materials such as disclosed in U.S. Pat. Nos. 6,303,238 and 6,310,360; U.S. Patent Application Publication Nos. 2002-0034656; 2002-0182441; 2003-0072964; and WO-02/074015.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. Nos. 5,844,363 and 6,602,540 B2, which are incorporated by reference in their entireties. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003-0230980 to Forrest et al., which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(ppy)_3$. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer. This may be accomplished by several ways: by doping the small molecule into the polymer either as a separate and distinct molecular species; or by incorporating the small molecule into the backbone of the polymer, so as to form a co-polymer; or by bonding the small molecule as a pendant group on the polymer. Other emissive layer materials and structures may be used. For example, a small molecule emissive material may be present as the core of a dendrimer.

Many useful emissive materials include one or more ligands bound to a metal center. A ligand may be referred to as "photoactive" if it contributes directly to the photoactive properties of an organometallic emissive material. A "photoactive" ligand may provide, in conjunction with a metal, the energy levels from which and to which an electron moves when a photon is emitted. Other ligands may be referred to as "ancillary." Ancillary ligands may modify the photoactive properties of the molecule, for example by shifting the energy levels of a photoactive ligand, but ancillary ligands do not directly provide the energy levels involved in light emission. A ligand that is photoactive in one molecule may be ancillary in another. These definitions of photoactive and ancillary are intended as non-limiting theories.

Electron transport layer 145 may include a material capable of transporting electrons. Electron transport layer 145 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2003-0230980 to Forrest et al., which is incorporated by reference in its entirety. Other electron transport layers may be used.

The charge carrying component of the electron transport layer may be selected such that electrons can be efficiently injected from the cathode into the LUMO (Lowest Unoccupied Molecular Orbital) energy level of the electron transport layer. The "charge carrying component" is the material responsible for the LUMO energy level that actually transports electrons. This component may be the base material, or it may be a dopant. The LUMO energy level of an organic material may be generally characterized by the electron affinity of that material and the relative electron injection efficiency of a cathode may be generally characterized in terms of the work function of the cathode material. This means that the preferred properties of an electron transport layer and the adjacent cathode may be specified in terms of the electron affinity of the charge carrying component of the ETL and the work function of the cathode material. In particular, so as to achieve high electron injection efficiency, the work function of the cathode material is preferably not greater than the electron affinity of the charge carrying component of the electron transport layer by more than about 0.75 eV, more preferably, by not more than about 0.5 eV. Similar considerations apply to any layer into which electrons are being injected.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436, 5,707,745, 6,548,956 B2 and 6,576,134 B2, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 145. Blocking layers may also be used to block excitons from diffusing out of the emissive layer. The theory and use of blocking layers is described in more detail in U.S. Pat. No. 6,097,147 and United States Patent Application Publication No. 2003-0230980 to Forrest et al., which are incorporated by reference in their entireties.

As used herein, and as would be understood by one skilled in the art, the term "blocking layer" means that the layer provides a barrier that significantly inhibits transport of charge carriers and/or excitons through the device, without suggesting that the layer necessarily completely blocks the charge carriers and/or excitons. The presence of such a blocking layer in a device may result in substantially higher efficiencies as compared to a similar device lacking a blocking layer. Also, a blocking layer may be used to confine emission to a desired region of an OLED.

Generally, injection layers are comprised of a material that may improve the injection of charge carriers from one layer, such as an electrode or an organic layer, into an adjacent organic layer. Injection layers may also perform a charge transport function. In device 100, hole injection layer 120 may be any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety. A hole injection layer may comprise a solution deposited material, such as a spin-coated polymer, e.g., PEDOT:PSS, or it may be a vapor deposited small molecule material, e.g., CuPc or MTDATA.

A hole injection layer (HIL) may planarize or wet the anode surface so as to provide efficient hole injection from the anode into the hole injecting material. A hole injection layer may also have a charge carrying component having HOMO (Highest Occupied Molecular Orbital) energy levels that favorably match up, as defined by their herein-described relative ionization potential (IP) energies, with the adjacent anode layer on one side of the HIL and the hole transporting layer on the opposite side of the HIL. The "charge carrying component" is the material responsible for the HOMO energy level that actually transports holes. This component may be the base material of the HIL, or it may be a dopant. Using a doped HIL allows the dopant to be selected for its electrical properties, and the host to be selected for morphological properties such as wetting, flexibility, toughness, etc. Preferred properties for the HIL material are such that holes can be efficiently injected from the anode into the HIL material. In particular, the charge carrying component of the HIL preferably has an IP not more than about 0.7 eV greater that the IP of the anode material. More preferably, the charge carrying component has an IP not more than about 0.5 eV greater than the anode material. Similar considerations apply to any layer into which holes are being injected. HIL materials are further distinguished from conventional hole transporting materials that are typically used in the hole transporting layer of an OLED in that such HIL materials may have a hole conductivity that is substantially less than the hole conductivity of conventional hole transporting materials. The thickness of the HIL of the present invention may be thick enough to help planarize or wet the surface of the anode layer. For example, an HIL thickness of as little as 10 nm may be acceptable for a very smooth anode surface. However, since anode surfaces tend to be very rough, a thickness for the HIL of up to 50 nm may be desired in some cases.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
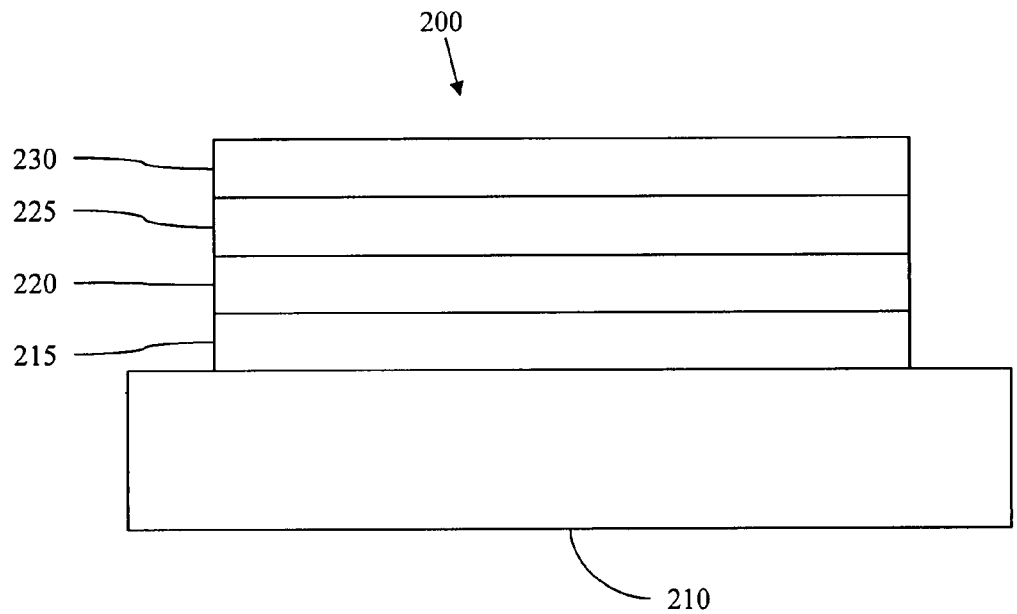
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJP. Other methods may also be used. The materials to be deposited may be modified to make them compatible with a particular deposition method. For example, substituents such as alkyl and aryl groups, branched or unbranched, may be used in small molecules to enhance their ability to undergo solution processing. Materials with asymmetric structures may have better solution processibility than those having symmetric structures, because asymmetric materials may have a lower tendency to recrystallize. Dendrimer substituents may be used to enhance the ability of small molecules to undergo solution processing.

The molecules disclosed herein may be substituted in a number of different ways without departing from the scope of the invention. For example, substituents may be added to a compound having three bidentate ligands, such that after the substituents are added, one or more of the bidentate ligands are linked together to form, for example, a tetradentate or hexadentate ligand. Other such linkages may be formed. It is believed that this type of linking may increase stability relative to a similar compound without linking, due to what is generally understood in the art as a "chelating effect."

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

In one aspect, the present invention provides organic electronic devices using phthalimide compounds having the formula:

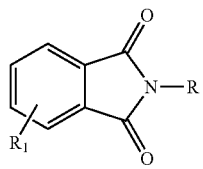

wherein $R_1$ represents one or more independently selected substitutions located on any position of the ring, wherein each substitution is a hydrogen, an alkyl moiety containing up to fifteen carbon atoms, or an aryl moiety, and wherein R is a phenyl group or a phthalimide-containing group.

The term "aryl moiety," as used herein, refers to structures containing at least one aromatic ring, including single-ring groups as well as polycyclic ring systems. The polycyclic rings may have two or more rings in which two atoms are common by two adjoining rings (i.e., the rings are "fused") wherein at least one of the rings is aromatic. Aryl moieties suitable for use as substituents in the present invention include phenyl, and oligoaryls such as naphthyl, biphenyl, and phenanthryl.

In some instances, R is a phthalimide-containing group represented by the formula:

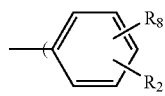

wherein $R_2$ represents one or more independently selected substitutions located on any position of the ring, wherein each substitution is hydrogen, an alkyl moiety containing up to fifteen carbon atoms, or an aryl moiety, wherein $R_8$ represents a substitution located on any position of the ring, wherein $R_8$ is phthalimide represented by the formula:

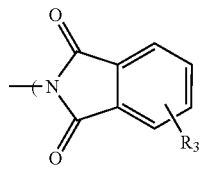

and wherein $R_3$ represents one or more independently selected substitutions located on any position of the ring, wherein each substitution is a hydrogen, an alkyl moiety containing up to fifteen carbon atoms, or an aryl moiety. The two phthalimide groups may be in ortho, meta, or para position on the central phenyl ring.

In some cases, the two phthalimide groups are in para position on the central phenyl ring. In some cases, each $R_3$ is selected from the group consisting of hydrogen, methyl, ethyl, propyl, isopropyl, butyl, isobutyl, tert-butyl, phenyl, naphthyl, biphenyl, and phenanthryl. In some cases, each $R_2$ is selected from the group consisting of hydrogen, methyl, ethyl, propyl, isopropyl, butyl, isobutyl, tert-butyl, phenyl, naphthyl, biphenyl, and phenanthryl. In some cases, each $R_1$ is selected from the group consisting of hydrogen, methyl, ethyl, propyl, isopropyl, butyl, isobutyl, tert-butyl, phenyl, naphthyl, biphenyl, and phenanthryl.

In some instances, R is a phthalimide-containing group represented by the formula:

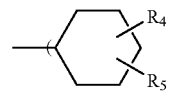

wherein $R_4$ represents one or more independently selected substitutions located on any position of the ring, wherein each substitution is hydrogen, an alkyl moiety containing up to fifteen carbon atoms, or an aryl moiety, and wherein $R_5$ represents a substitution located on any position of the ring, wherein $R_5$ is represented by the formula:

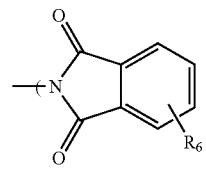

wherein $R_6$ represents one or more independently selected substitutions located on any position of the ring, wherein each substitution is hydrogen, an alkyl moiety containing up to fifteen carbon atoms, or an aryl moiety. The two phthalimide groups may be in ortho, meta, or para position on the cyclohexane ring.

In some cases, the two phthalimide groups are in ortho position on the cyclohexane ring. In some cases, each $R_4$ is independently selected from the group consisting of hydrogen, methyl, ethyl, propyl, isopropyl, butyl, isobutyl, tert-butyl, phenyl, naphthyl, biphenyl, and phenanthryl. In some cases, each $R_6$ is independently selected from the group consisting of hydrogen, methyl, ethyl, propyl, isopropyl, butyl, isobutyl, tert-butyl, phenyl, naphthyl, biphenyl, and phenanthryl.

In some instances, R is a phenyl ring, with or without alkyl moiety substitutions containing up to fifteen carbon atoms, or aryl moiety substitutions. In some cases, the substitutions may be selected from the group consisting of hydrogen, methyl, ethyl, propyl, isopropyl, butyl, isobutyl, tert-butyl, phenyl, naphthyl, biphenyl, and phenanthryl. In some cases, the phenyl ring has no substitutions.

Examples of phthalimide compounds suitable for use in the present invention include the following:

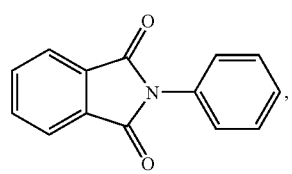

P-1p

-continued

P-2p
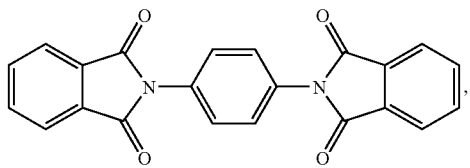

NPP
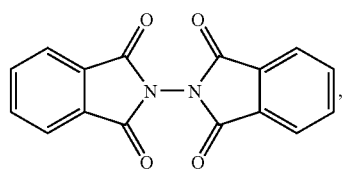

TMPP
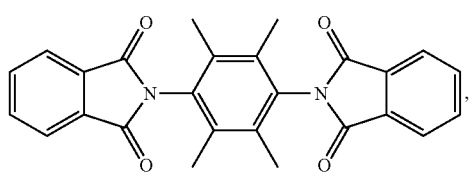

TMPP*
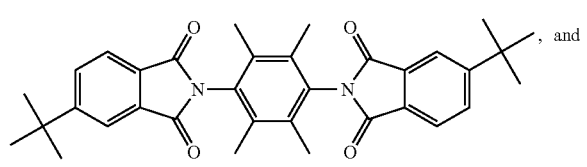
, and

CH-2p
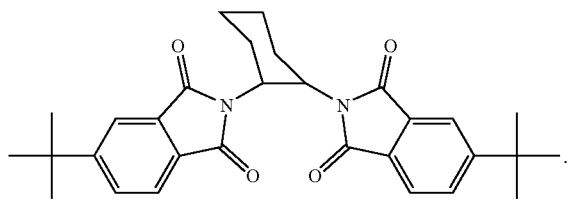

In another aspect, the present invention provides organic electronic devices using phthalimide compounds having the formula:

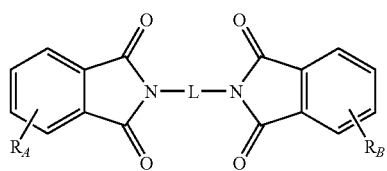

wherein $R_A$ represents one or more independently selected substitutions located on any position of the ring, wherein each substitution is a hydrogen, an alkyl moiety containing up to fifteen carbon atoms, or an aryl moiety, wherein $R_B$ represents one or more independently selected substitutions located on any position of the ring, wherein each substitution is a hydrogen, an alkyl moiety containing up to fifteen carbon atoms, or an aryl moiety, and wherein L is a 6-membered ring or a direct bond between the two phthalimide groups.

In some instances, L is a cyclohexane ring represented by the formula:

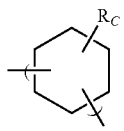

wherein $R_C$ represents one or more independently selected substitutions located on any position of the ring, wherein each substitution is a hydrogen, an alkyl moiety containing up to fifteen carbon atoms, or an aryl moiety, and wherein the two phthalimide groups are in ortho, meta, or para position on the cyclohexane ring.

In some cases, the two phthalimide groups on the cyclohexane ring are in ortho position. In some cases, each of $R_C$ on the cyclohexane is hydrogen. In some cases, each $R_A$ is independently selected from the group consisting of hydrogen, methyl, ethyl, propyl, isopropyl, butyl, isobutyl, tert-butyl, phenyl, naphthyl, biphenyl, and phenanthryl. In some cases, each $R_B$ is independently selected from the group consisting of hydrogen, methyl, ethyl, propyl, isopropyl, butyl, isobutyl, tert-butyl, phenyl, naphthyl, biphenyl, and phenanthryl. In some cases, each $R_A$ is a tent-butyl and each $R_B$ is a tert-butyl.

In some instances, L is a phenyl ring represented by the formula:

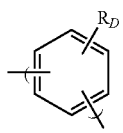

wherein $R_D$ represents one or more independently selected substitutions located on any position of the ring, wherein each substitution is a hydrogen, an alkyl moiety containing up to fifteen carbon atoms, or an aryl moiety, and wherein the two phthalimide groups are in ortho, meta, or para position on the phenyl ring.

In some cases, the two phthalimide groups on the phenyl ring are in para position. In some cases, each of $R_D$ on the cyclohexane is hydrogen. In some cases, each of $R_D$ on the cyclohexane is methyl. In some cases, each $R_A$ is independently selected from the group consisting of hydrogen, methyl, ethyl, propyl, isopropyl, butyl, isobutyl, tert-butyl, phenyl, naphthyl, biphenyl, and phenanthryl. In some cases, each $R_B$ is independently selected from the group consisting of hydrogen, methyl, ethyl, propyl, isopropyl, butyl, isobutyl, tert-butyl, phenyl, naphthyl, biphenyl, and phenanthryl. In some cases, each $R_A$ is a tert-butyl and each $R_B$ is a tert-butyl.

The phthalimide compounds disclosed herein are electron transporters with large HOMO-LUMO gaps, high triplet energies, large reduction potentials, and/or thermal and chemical stability. As such, these phthalimide compounds are suitable for use in any of various organic electronic devices, such as OLEDs and solar cells. In OLEDs, the phthalimide compounds may be used in any of the various layers of the OLED. For example, the phthalimide compounds may be used in the emissive layer (as a host material, for instance). In another example, the phthalimide compounds may be used in the hole blocking layer (as a hole blocking material, for instance). In another example, the phthalimide compounds may be used in an electron blocking layer. The phthalimide compounds may also be used in solar cells. For example, the compounds may be used in the exciton blocking layer of a solar cell.

Compound Synthesis Examples

As shown in the reactions schemes below, synthesis of the target compounds (6-9) was performed in one step from commercially available phthalic anhydride 1; 4-tert-butyl phthalic anhydride 2; phenyl-1,2-diamine 3; 2,3,5,6-tetramethyl-phenyl-1,2-diamine 4; and cyclohexane-1,4-diamine 5. All reactions were conducted inside a microwave reactor in a solvent free environment. Phthalimide compounds 6 and 7 were synthesized by irradiating the mixtures of anhydride 1 with either amine 3 or amine 4 in two different reactions. The tert-butyl phthalimide compounds 8 and 9 were made in a similar fashion by reacting the tert-butyl anhydride 2 with either amine 4 or amine 5 under microwave conditions separately.

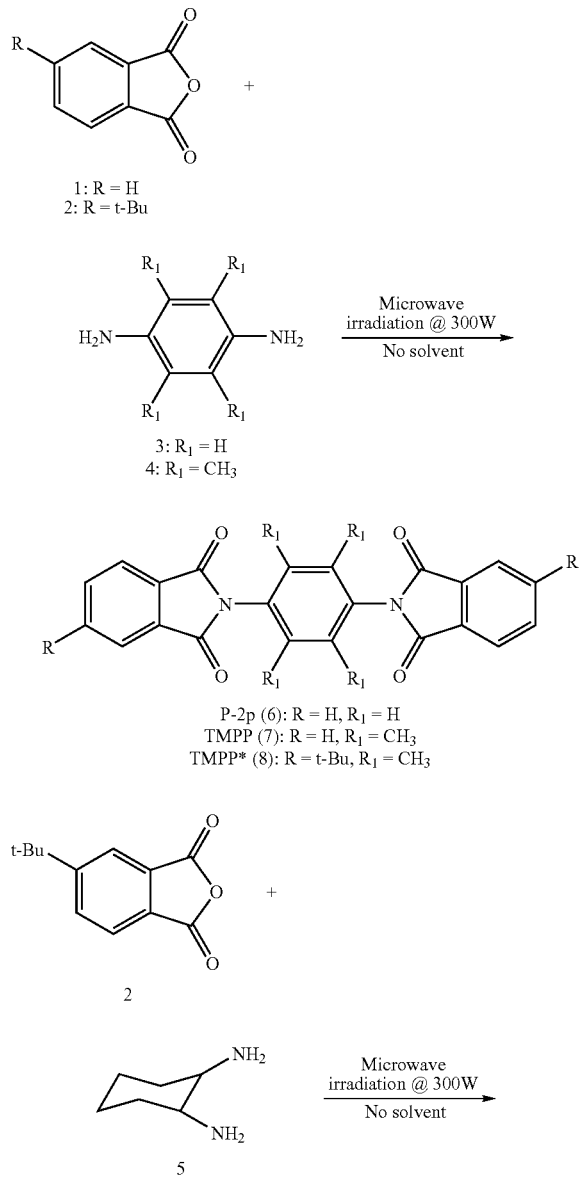

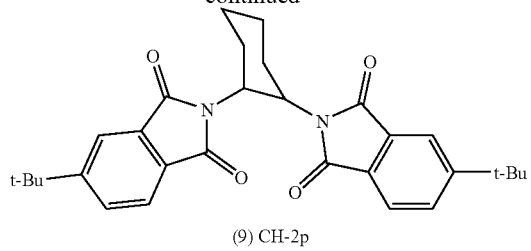

(9) CH-2p

General Procedure. The reactant anhydrides and the amines were mixed in two different ways before synthesis. These reactants were either dry mixed and ground to fine powders in a mortar and pestle or mixed with dichloromethane, stirred for ten minutes, and then concentrated in vacuo.

Phenyl-1,4-bis-phthalimide (Compound P-2p). A mixture of phenyl-1,2-diamine 3 (1 equiv) and phthalic anhydride 1 (3 equiv) was subjected to microwave (300 W) irradiation at 250° C. for 40 minutes. The dark colored insoluble material was then sublimed at 265° C. to give off-white crystals of phthalimide compound P-2p in 80% yield. Analysis Data: $^1$H NMR (250 MHz, CDCl$_3$): δ 8.01 (dd, 4H), δ 7.80 (dd, 4H). Elemental analysis results: C=71.55; H=3.20; N=7.61, compared to calculated values of C=71.74; H=3.28; N=7.61 for $C_{22}H_{12}N_2O_4$.

2,3,5,6-tetramethyl-phenyl-1,4-(bis-phthalimide) (Compound TMPP). A solid solution of 2,3,5,6-tetramethyl-phenyl-1,2-diamine 4 (1 equiv) and phthalic anhydride 1 (3 equiv) was placed inside the 300 W microwave reactor and heated to 250° C. for 40 minutes. The dark brown material was sublimed at 285° C. to afford light yellow crystals of phthalimide compound TMPP in 80% yield. Analysis Data: Mp (DSC) 462° C. $^1$H NMR (250 MHz, CDCl$_3$): δ 8.01 (dd, 4H), δ 7.80 (dd, 4H), δ 1.57 (s, 12H). Elemental analysis results: C=73.70; H=4.66; N=6.60, compared to calculated values of C=73.57; H=4.75; N=6.60 for $C_{26}H_{20}N_2O_4$.

2,3,5,6-tetramethyl-phenyl-1,4-bis-(4-tert-butylphthalimide) (Compound TMPP*). A mixture of 2,3,5,6-tetramethyl-phenyl-1,2-diamine 4 (1 equiv) and 4-t-butyl phthalic anhydride 2 (3 equiv) was placed inside the microwave reactor (300 W) and irradiated for 40 minutes at 120° C. The yellow colored crude was passed through a short column of silica gel in dichloromethane. Concentration of this elute followed by a flash chromatographic purification of the crude (SiO$_2$, dichloromethane) gave phthalimide compound TMPP* as white powder in 85% yield. Analysis Data: Mp (DSC) 413° C., T$_g$ (DSC) 88° C., T$_c$ (DSC) 189° C. $^1$H NMR (360 MHz, CDCl$_3$): δ 8.01 (d, J=0.003 Hz, 2H), δ 7.90 (dd, J=0.043 Hz, 4H), δ 2.09 (s, 12H), δ 1.43 (s, 18H). Elemental analysis results: C=76.31; H=6.75; N=5.31, compared to calculated values of C=76.09; H=6.76; N=5.22 for $C_{34}H_{36}N_2O_4$.

1,2-bis-(4-tert-butylphthalimide)-cyclohexane (Compound CH-2p). Cyclohexane-1,4-diamine 5 (1 equiv) was mixed with 4-tert-butyl phthalic anhydride 2 (3 equiv) in dichloromethane (20 ml). The reaction mixture was then stirred for 10 minutes, concentrated in vacuo, and subjected to microwave (300 W) reaction for 30 minutes at 250° C. The dark yellow crude was then passed through a silica gel filter, concentrated, and subjected to flash chromatography (silica gel) in dichloromethane to give pure yellow crystals of phthalimide compound CH-2p in 60% yield. Analysis Data: Mp (DSC) 388° C., T$_g$ (DSC) 88° C. $^1$H NMR (360 MHz, CDCl$_3$): δ 7.70 (br m, 6H), δ 5.07 (m, J=0.008 Hz, 2H), δ 2.37 (br m, 2H), δ 1.88 (br m, 4H), δ 1.57 (br m, 2H), δ 1.31 (s, 18H). Elemental analysis results: C=74.11; H=6.99; N=5.78, compared with calculated values of C=74.05; H=7.04; N=5.76 for $C_{30}H_{34}N_2O_4$.

Solution photophysics data of various of the phthalimide compounds are shown in Table 1 below. These data indicate that the phthalimide compounds have high triplet energies and lifetimes in the millisecond range.

TABLE 1

| Compound | $\lambda_{max}$ (298K) (nm) | $\Phi_S$ | $E_s$ (nm/eV) | $\tau_S$ (ns) | $\lambda_{max}$ (77K) (nm) | $E_T$ (nm/eV) | $\tau_T$ (ms) |
|---|---|---|---|---|---|---|---|
| NPP | — | — | 313/3.96 | — | 410, 420, 442 | 410/3.02 | 667 |
| TMPP | — | — | 313/3.96 | — | 426, 448 | 426/2.91 | 360 |
| TMPP* | 447 | — | 318/3.90 | — | 316, 445, 380, 456 | 430/2.9 | 450 |
| P-2p | — | — | 313/3.96 | — | 355, 432, 448 | 432/2.87 | 349 |
| P-1p | 495 | — | 322/3.85 | — | 360, 449 | 449/2.76 | 224 |
| CH-2p | 400 | 5.2E−05 | 318/3.90 | <5 | 381, 452 | 452/2.74 | 590 |

Device Examples

Phthalimide compounds TMPP and TMPP* were used in fabricating OLEDs. All OLEDs were fabricated on ITO-coated glass substrates and circuit patterns were photolithographically imprinted on the substrates as 2 mm wide stripes with 1 mm spacings. Surface resistivity of the ITO coating was measured to be approximately $20\Omega^{-1}$. The ITO coated substrates were then rinsed with acetone, sonicated in soap-water solution, and boiled in trichloroethylene, acetone, and ethanol for 5 minutes each. Afterwards, the substrates were treated for ten minutes in the UV-ozone cleaning chamber.

The OLEDs were fabricated inside a high vacuum chamber (Kurt J. Lesker) equipped with a cryo pump, two crystal monitors, and two power sources. Organic films were thermally evaporated onto the ITO substrates from tantalum boats at pressures between 3-4 µtorr. Deposition rates for all the organic materials were maintained to be between 2-4 Å/s at all times. Prior to the deposition of the cathode, the chamber was vented with nitrogen and shadow masks consisting of 2 mm stripes were placed onto the substrates. Once the pressure reached 3.0 µtorr, 10 Å of lithium fluoride (LiF) was deposited at 0.2 Å/s rate followed by a 1200 Å layer of aluminum at rates between 4-5 Å/s.

Three sets of devices (A, B, and C) were fabricated on the ITO substrates having the general architecture: a 400 Å layer of NPD as the hole transport layer; a 250 Å layer of host:dopant material as the emissive layer; a 150 Å layer of a hole blocking material as the hole blocking layer; a 150 Å layer of $Alq_3$ as the electron transport layer; and LiF (10 Å)/Al (1200 Å) as the cathode.

In device set A, fac-tris(2-phenylpyridinato-N,$C^2$) iridium (III) (Irppy) was used as the dopant in the emissive layer. In Device A1 (control), CBP was used as the host in the emissive layer, and BCP was used as the hole blocking material. In Device A2, CBP was used as the host in the emissive layer, and TMPP* was used as the hole blocking material. In Device A3, TMPP* was used as the host in the emissive layer, and BCP was used as the hole blocking layer.

In device set B, bis(2-phenylquinolyl-N,$C^2$) iridium(III) (PQIr) was used as the dopant in the emissive layer. In Device B1 (control), CBP was used as the host in the emissive layer, and BCP was used as the hole blocking material. In Device B2, CBP was used as the host in the emissive layer, and TMPP* was used as the hole blocking material. In Device B3, TMPP* was used as the host in the emissive layer, and BCP was used as the hole blocking material. In Device B4, TMPP* was used as both the host in the emissive material and as the hole blocking material.

In device set C, PQIr was used as the dopant in the emissive layer. Device C1 (control) is the same as device B1. In Device C2, CBP was used as the host in the emissive layer, and TMPP was used as the hole blocking material. In Device C3, TMPP was used as the host in the emissive layer, and BCP was used as the hole blocking material. In Device C4, TMPP was used as both the host in the emissive material and as the hole blocking material.

All OLEDs were tested in room temperature and pressure in an open atmosphere. LabVIEW program was used to measure the brightness and current-voltage (I-V) characteristics of the devices. A Keithley 2400 source meter was used to power-up the OLEDs and light emitted from the front of the devices were collected through a UV-818 Si photocathode equipped with a Newport 1835-C optical meter. Electroluminescence spectra of the devices were recorded using a spectrofluorometer, model C-60SE.

Figure 3:
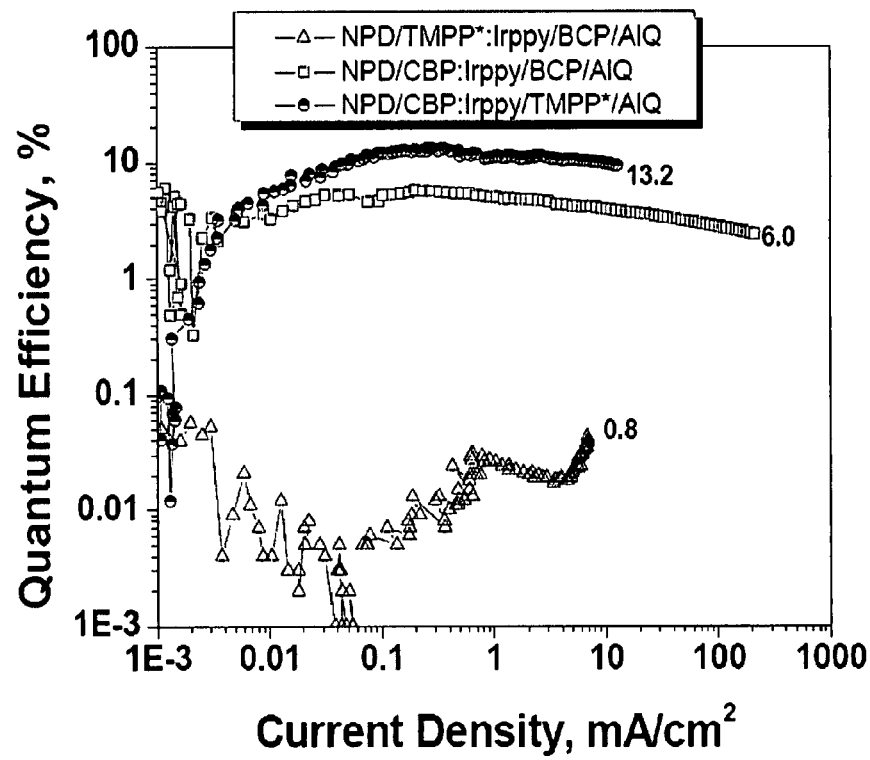
FIG. 3 shows a plot of quantum efficiency v. current density for devices A1-A3.

FIG. 3 shows a plot of quantum efficiency v. current density of devices A1-A3. Device A3 (triangles), which uses TMPP* as the host and Irppy as the dopant in the emissive layer, has low quantum efficiency because of electron transfer quenching of the host by the dopant. Device A2 (half-filled circles), which uses TMPP* in the hole blocking layer, has high efficiency because of the hole/exciton blocking ability of TMPP*. In this case, Device A2 has more than twice the efficiency of control Device A1 (squares).

Figure 4:
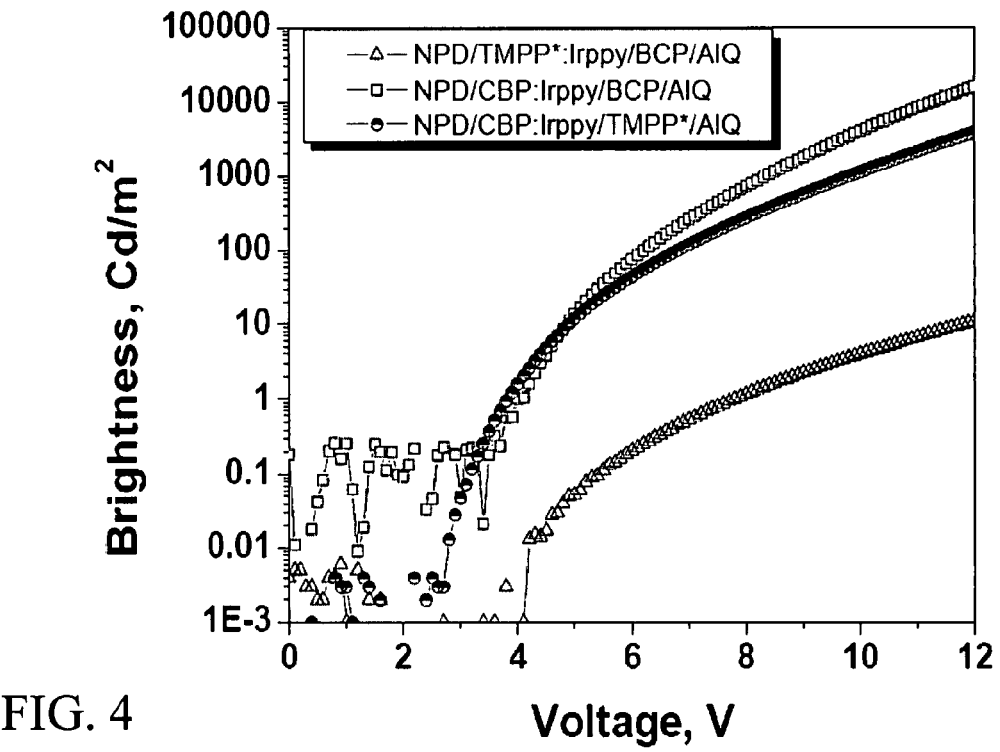
FIG. 4 shows a plot of brightness v. voltage for devices A1-A3.

FIG. 4 shows a plot of brightness v. voltage of devices A1-A3. Device A3 is dim because quenching of the TMPP* host by the Irppy dopant increases the non-radiative relaxation of the excited dopants. Device A2 is bright because the hole/exciton blocking by TMPP* increases the balanced recombination and decreases the non-radiative relaxation of the excitons. In this case, Device A2 is dimmer than control Device A1, but both have approximately the same turn-on voltages.

Figure 5:
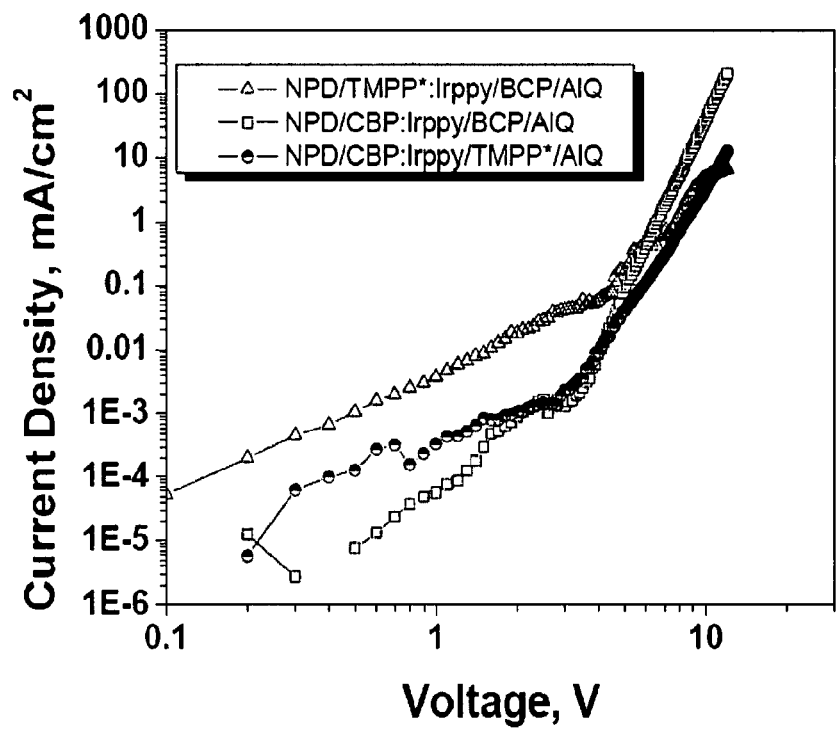
FIG. 5 shows a plot current density v. voltage for device A1-A3.

FIG. 5 shows a plot current density v. voltage of devices A1-A3. Device A3 has current leakage and a high turn-on voltage. Electron transfer from the excited dopant to the TMPP* host creates excess holes. Because I-V is dominated by electron flow, the electrons have low mobility, and excess holes have to wait longer to recombine with electrons. Also, excess holes in the space charge limited (SCLC) region may create a barrier for incoming electrons by slightly changing the internal electric field. These factors could prolong the turn-on voltage of the device. In comparison, Device A2 shows minimal shorts or current leakage. In this case, the I-V shape and turn-on voltage of Device A2 is comparable to control Device A1.

Figure 6:
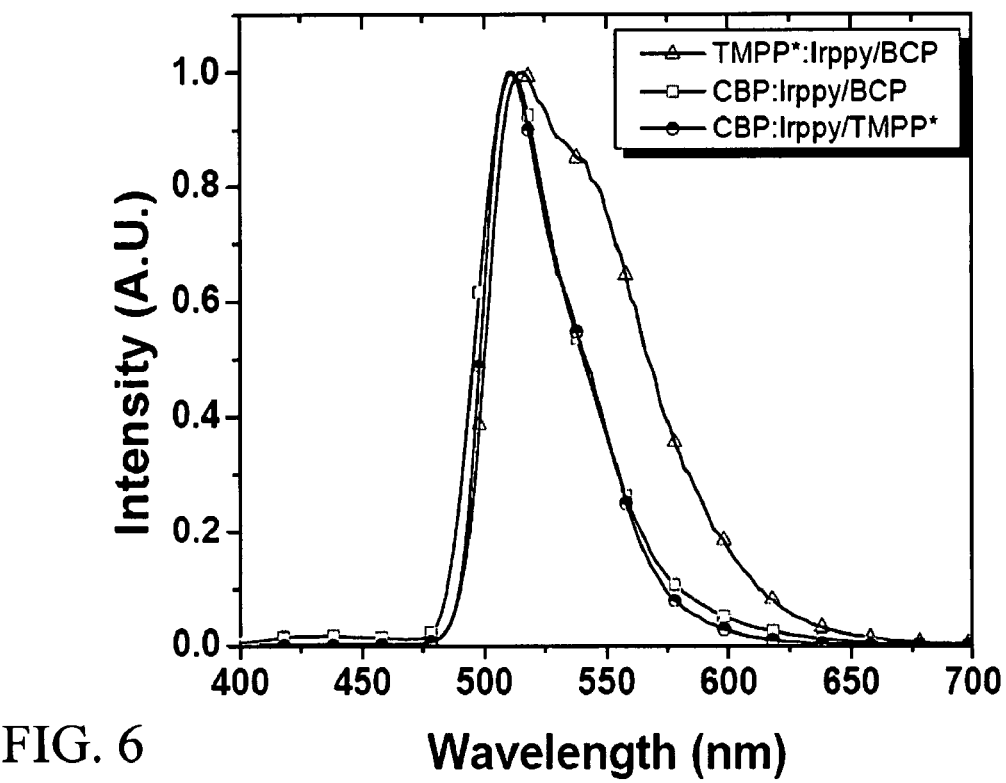
FIG. 6 shows the electroluminescent spectra for devices A1-A3.

FIG. 6 shows the electroluminescent spectra of devices A1-A3. Device A3 exhibits a $\lambda_{max}$=515 nm attributable to Irppy, with another $\lambda_{max}$=541, possibly attributable to emission from exciplexes formed between the TMPP* and NPD.

Device A2 exhibits a $\lambda_{max}$=512 nm attributable to Irppy. Electroluminescence is only observed from the dopant. This data demonstrates that TMPP* performs well as an electron transporter and a hole blocker.

Figure 7:
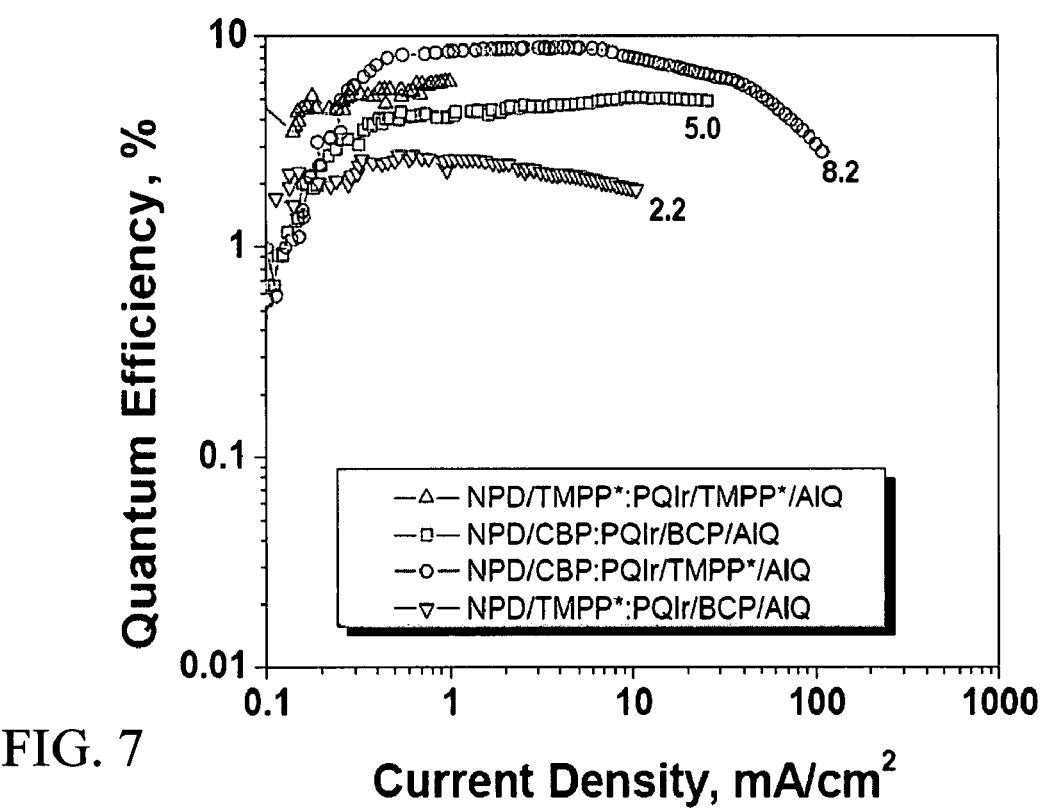
FIG. 7 shows a plot of quantum efficiency v. current density for devices B1-B4.

FIG. 7 shows a plot of quantum efficiency v. current density of devices B1-B4. Device B3 (inverted triangles), which uses TMPP* as the host and PQIr as the dopant in the emissive layer, has low quantum efficiency because of electron transfer quenching of the host by the dopant. Device B4 (upright triangles), which uses TMPP* as a host in the emissive material and as the hole blocking material, has very low quantum efficiency and a very short lifetime. In comparison to control Device B1 (squares), Device B2 (circles) is very efficient because of the hole/exciton blocking capability of TMPP*. In this case, Device B2 is more than 1.5 times efficient as control Device B1.

Figure 8:
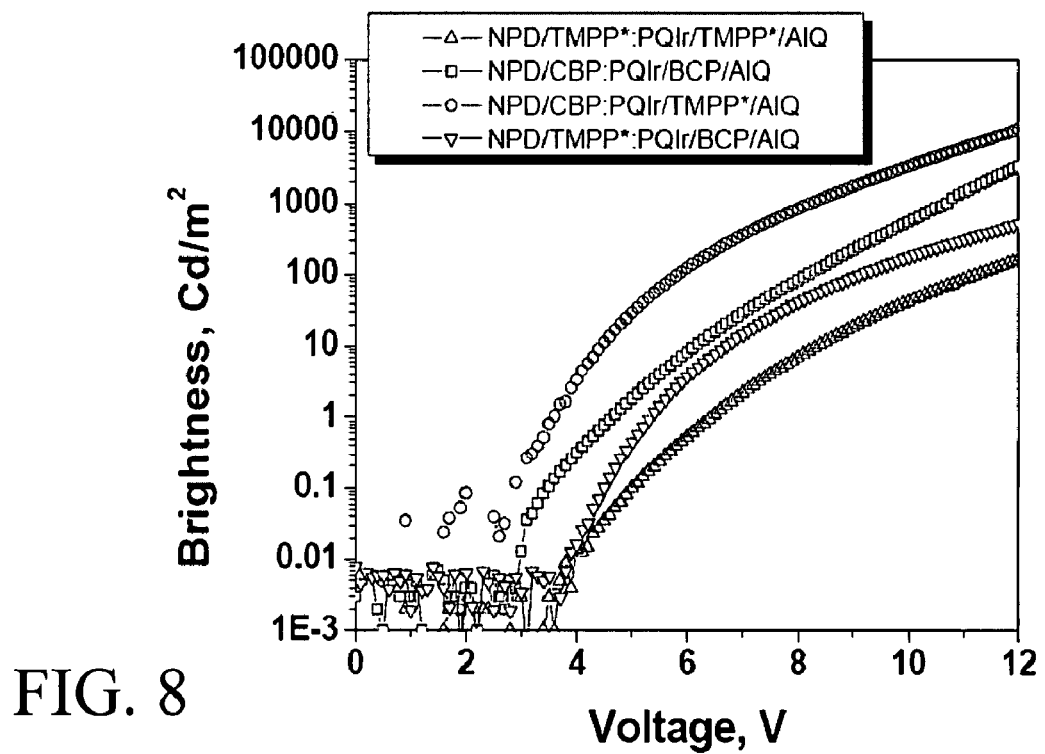
FIG. 8 shows a plot of brightness v. voltage for devices B1-B4.

FIG. 8 shows a plot of brightness v. voltage of devices B1-B4. Device B3 is dim because quenching of the TMPP* host by the Irppy dopant increases the non-radiative relaxation of the excited dopants. Likewise, Device B4 is dim because of the quenching effect. Exciplexes (emissive or non-emissive) formed between the TMPP* and NPD may also serve to decrease efficiency. Device B2 is bright and efficient because of the hole/exciton blocking ability of TMPP*, which increases the balanced recombination and decreases the non-radiative relaxation of the excitons. Because the triplet energy of TMPP* is much higher than the triplet energy of PQIr, energy transfer is more efficient and the device is brighter. In this case, Device B2 is brighter than control Device B1.

Figure 9:
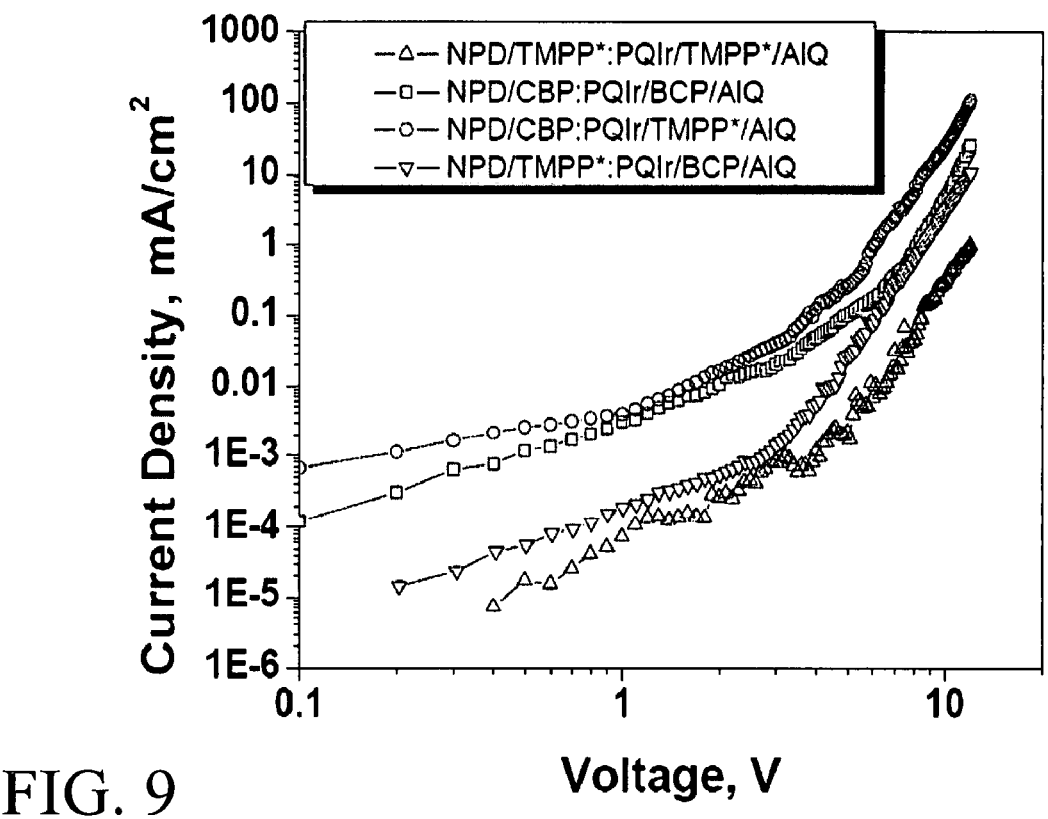
FIG. 9 shows a plot of current density v. voltage for devices B1-B4.
Figure 10:
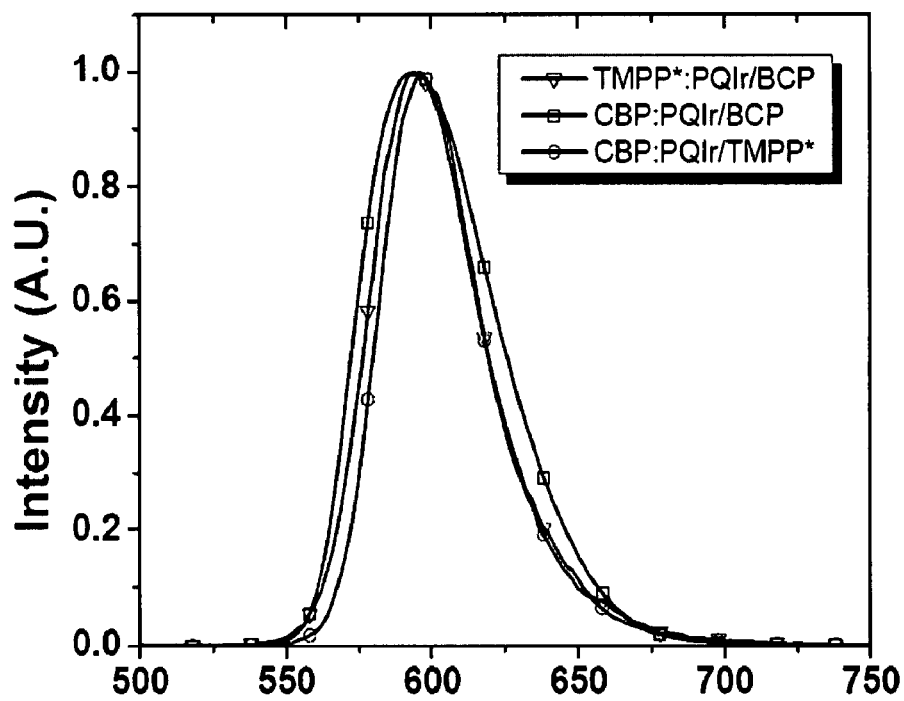
FIG. 10 shows the electroluminescent spectra for devices B1-B4.

FIG. 9 shows a plot of current density v. voltage of device B1-B4. The I-V shape and turn-on voltage of Device B2 is similar to control Device B1. The I-V plot of Device 4 shows a shortage, but the I-V plot of Device 3 appears good. FIG. 10 shows the electroluminescent spectra of devices B1-B3. Each of these devices exhibit PQIr emission only.

Figure 11:
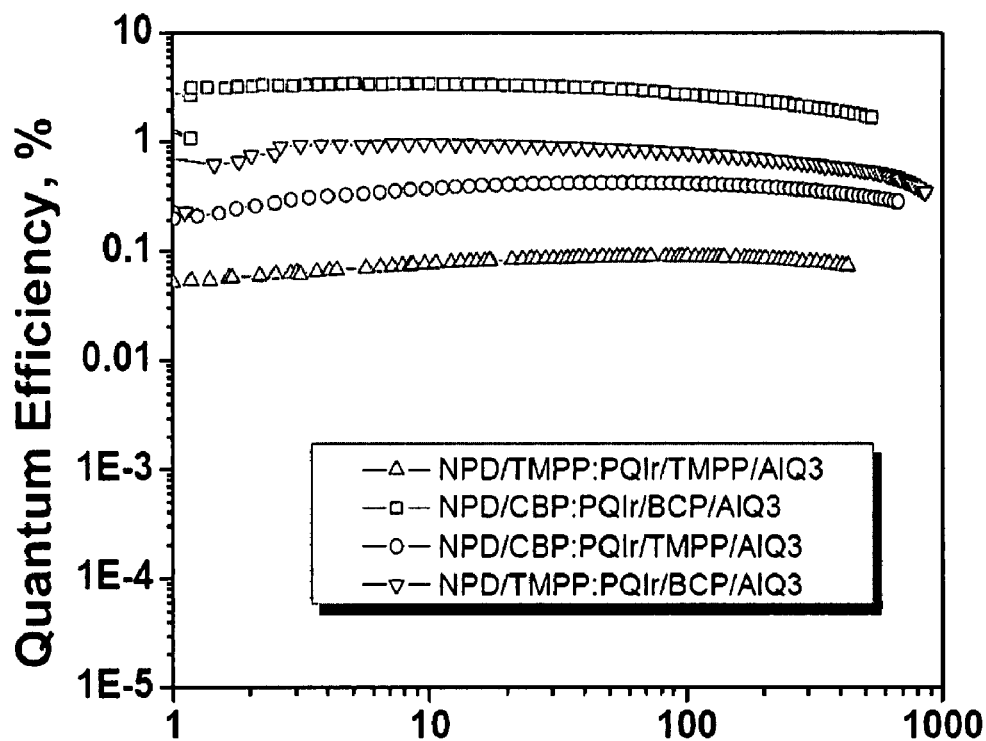
FIG. 11 shows a plot of quantum efficiency v. current density for devices C1-C4.

FIG. 11 shows a plot of quantum efficiency v. current density of devices C1-C4. Device C3 (inverted triangles), which uses TMPP as the host and PQIr as the dopant in the emissive layer, has low quantum efficiency because of electron transfer quenching of the host by the dopant. Device B4 (upright triangles), which uses TMPP as a host in the emissive material and as the hole blocking material, also has low quantum efficiency because of electron transfer quenching of the host by the dopant. Also, because TMPP has no glass transition temperature $T_g$, crystalline islands may form upon deposition, which reduces energy transfer from TMPP to PQIr, allowing emission from $Alq_3$ to become dominant.

Figure 12:
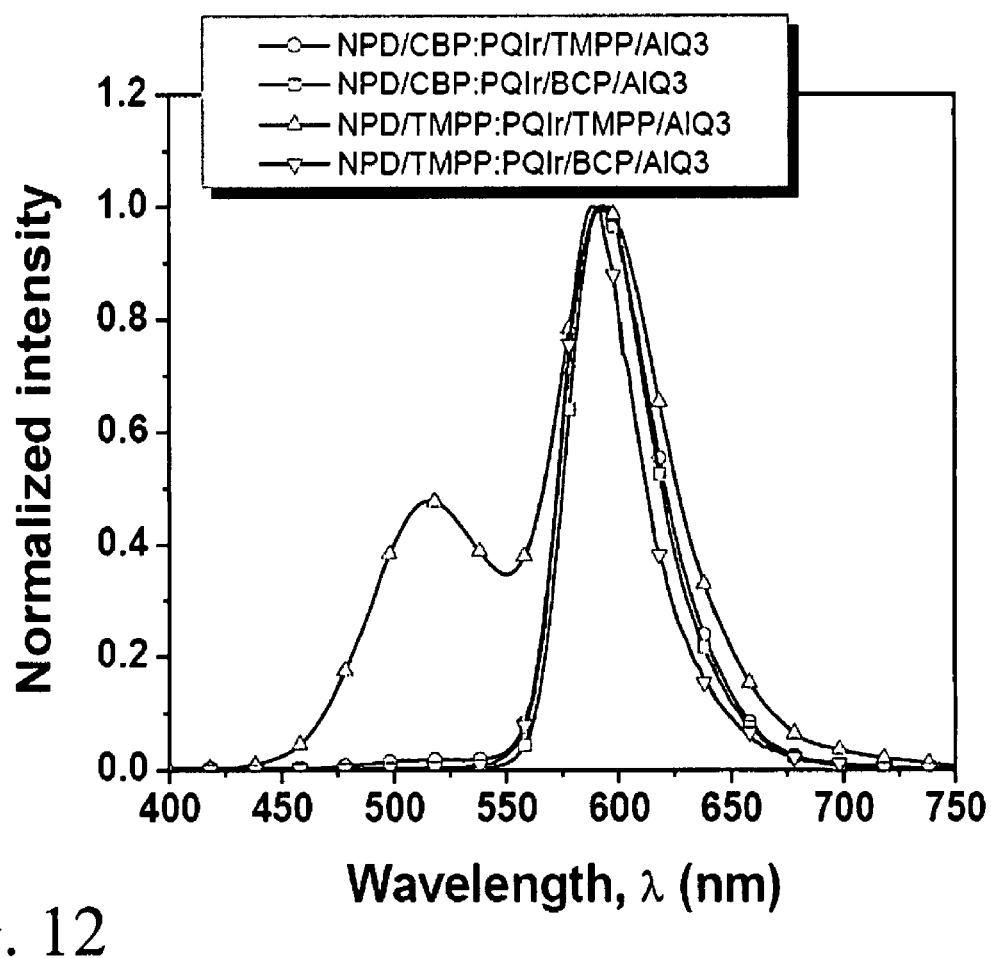
FIG. 12 shows the electroluminescent spectra for devices C1-C4.

FIG. 12 shows the electroluminescent spectra of devices C1-C4. Device C1-C3 exhibit PQIr emission only ($\lambda_{max}$=595 nm). Device C4 exhibits $Alq_3$ emission ($\lambda_{max}$=510 nm) in addition to PQIr emission.

The above results demonstrate that using the phthalimide compounds disclosed herein in organic light-emitting devices can improve the performance and efficiency of the devices.

Material Definitions

As used herein, abbreviations refer to materials as follows:
CBP: 4,4'-N,N'-dicarbazole-biphenyl
m-MTDATA 4,4',4''-tris(3-methylphenylphenlyamino)triphenylamine
$Alq_3$: 8-tris-hydroxyquinoline aluminum
BPhen: 4,7-diphenyl-1,10-phenanthroline
n-BPhen: n-doped BPhen (doped with lithium)
$F_4$-TCNQ: tetrafluoro-tetracyano-quinodimethane
p-MTDATA: p-doped m-MTDATA (doped with $F_4$-TCNQ)
$Ir(ppy)_3$: tris(2-phenylpyridine)-iridium
$Ir(ppz)_3$: tris(1-phenylpyrazoloto,N,C(2')iridium(III)
BCP: 2,9-dimethyl-4,7-diphenyl-1,10-phenanthroline
TAZ: 3-phenyl-4-(1'-naphthyl)-5-phenyl-1,2,4-triazole
CuPc: copper phthalocyanine.
ITO: indium tin oxide
NPD: N,N'-diphenyl-N—N'-di(1-naphthyl)-benzidine
TPD: N,N'-diphenyl-N—N'-di(3-toly)-benzidine
BAlq: aluminum(III)bis(2-methyl-8-hydroxyquinolinato)-4-phenylphenolate
mCP: 1,3-N,N-dicarbazole-benzene
DCM: 4-(dicyanoethylene)-6-(4-dimethylaminostyryl-2-methyl)-4H-pyran
DMQA: N,N'-dimethylquinacridone

What is claimed is:

1. An organic light-emitting device comprising:
an anode;
a cathode; and
an emissive layer disposed between the anode and the cathode, wherein the emissive layer comprises a phosphorescent dopant and a phthalimide compound as a host having the formula:

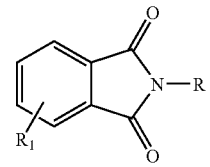

wherein $R_1$ represents one or more independently selected substitutions located on any position of the ring, wherein each substitution is a hydrogen, an alkyl moiety containing up to fifteen carbon atoms, or an aryl moiety, and
wherein R is represented by one of the following formula:

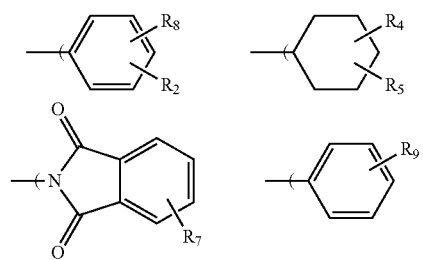

wherein $R_2$, $R_3$, $R_4$, $R_7$, and $R_9$ each represents one or more independently selected substitutions located on any position of the ring, wherein each substitution is hydrogen, an alkyl moiety containing up to fifteen carbon atoms, or an aryl moiety,
wherein $R_5$ and $R_8$ each represents a substitution located on any position of the ring, wherein $R_5$ and $R_8$ is represented by the formula:

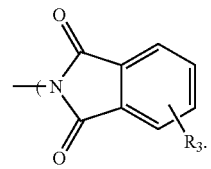

2. The device of claim 1, wherein R is represented by the formula:

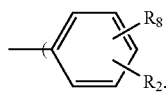

3. The device of claim 2, wherein each $R_3$ is selected from the group consisting of hydrogen, methyl, ethyl, propyl, isopropyl, butyl, isobutyl, and tert-butyl.

4. The device of claim 2, wherein each $R_2$ is selected from the group consisting of hydrogen, methyl, ethyl, propyl, isopropyl, butyl, isobutyl, and tert-butyl.

5. The device of claim 2, wherein each $R_3$ is selected from the group consisting of hydrogen, methyl, ethyl, propyl, isopropyl, butyl, isobutyl, tert-butyl, phenyl, naphthyl, biphenyl, and phenanthryl.

6. The device of claim 2, wherein each $R_2$ is selected from the group consisting of hydrogen, methyl, ethyl, propyl, isopropyl, butyl, isobutyl, tert-butyl, phenyl, naphthyl, biphenyl, and phenanthryl.

7. The device of claim 2, wherein the two phthalimide groups are in para position on the phenyl ring.

8. The device of claim 1, wherein each $R_1$ is selected from the group consisting of hydrogen, methyl, ethyl, propyl, isopropyl, butyl, isobutyl, and tert-butyl.

9. The device of claim 1, wherein each $R_1$ is selected from the group consisting of hydrogen, methyl, ethyl, propyl, isopropyl, butyl, isobutyl, tert-butyl, phenyl, naphthyl, biphenyl, and phenanthryl.

10. The device of claim 1, wherein R is represented by the formula:

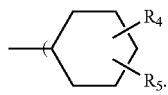

11. The device of claim 10, wherein the two phthalimide groups are in ortho position on the cyclohexane ring.

12. The device of claim 10, wherein each $R_4$ is independently selected from the group consisting of hydrogen, methyl, ethyl, propyl, isopropyl, butyl, isobutyl, and tert-butyl.

13. The device of claim 10, wherein each $R_6$ is independently selected from the group consisting of hydrogen, methyl, ethyl, propyl, isopropyl, butyl, isobutyl, and tert-butyl.

14. The device of claim 10, wherein each $R_4$ is independently selected from the group consisting of hydrogen, methyl, ethyl, propyl, isopropyl, butyl, isobutyl, tert-butyl, phenyl, naphthyl, biphenyl, and phenanthryl.

15. The device of claim 10, wherein each $R_6$ is independently selected from the group consisting of hydrogen, methyl, ethyl, propyl, isopropyl, butyl, isobutyl, tert-butyl, phenyl, naphthyl, biphenyl, and phenanthryl.

16. The device of claim 1, wherein R is represented by the formula:

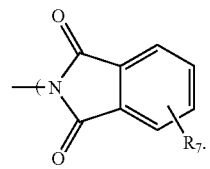

17. The device of claim 16, wherein each $R_7$ is independently selected from the group consisting of: hydrogen, methyl, ethyl, propyl, isopropyl, butyl, isobutyl, and tert-butyl.

18. The device of claim 16, wherein each $R_7$ is independently selected from the group consisting of: hydrogen, methyl, ethyl, propyl, isopropyl, butyl, isobutyl, tert-butyl, phenyl, naphthyl, biphenyl, and phenanthryl.

19. The device of claim 1, wherein R is represented by the formula:

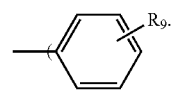

20. The device of claim 19, wherein each $R_9$ is hydrogen.

21. The device of claim 1, wherein the phthalimide compound is a bis-phthalimide.

22. The device of claim 1, wherein the phthalimide compound is selected from the group consisting of:

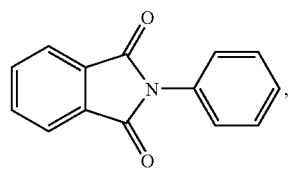

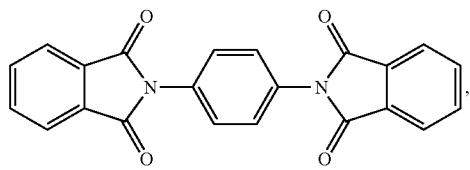

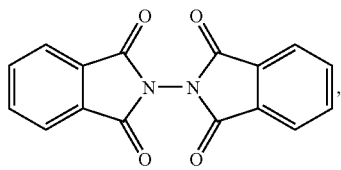

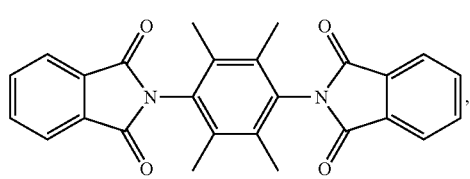

-continued
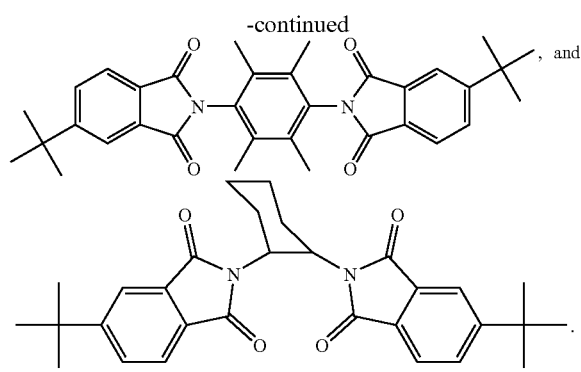
, and
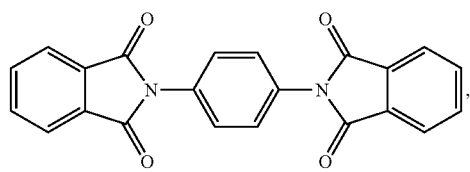
.
23. The device of claim 1, wherein the phthalimide compound is selected from the group consisting of:
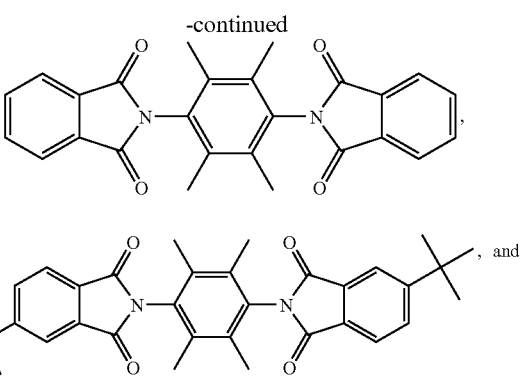
, and
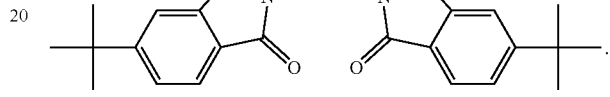
.
* * * * *